United States Patent [19]

Kalina

[11] Patent Number: 4,978,618
[45] Date of Patent: Dec. 18, 1990

[54] ALCOHOL PRODUCTION
[75] Inventor: Vladimir Kalina, Lausanne, Switzerland
[73] Assignee: Nestec S.A., Vevey, Switzerland
[21] Appl. No.: 140,473
[22] Filed: Jan. 4, 1988
[30] Foreign Application Priority Data Jan. 16, 1987 [CH] Switzerland .................. 149/87-0

[51] Int. Cl.$^5$ .................... C12P 7/14; C12N 1/18
[52] U.S. Cl. .................... 435/162; 435/255;
435/256; 435/800; 435/813; 435/819
[58] Field of Search ............... 435/161, 162, 163, 813,
435/819, 255, 256, 801, 818, 800; 426/11, 13,
15, 16, 30

[56] References Cited

U.S. PATENT DOCUMENTS

| | | | |
|---|---|---|---|
| 3,234,026 | 2/1966 | Coutls | 426/16 |
| 4,310,629 | 1/1982 | Muller et al. | 435/162 |
| 4,346,113 | 8/1982 | Faust et al. | 435/161 |
| 4,383,040 | 5/1983 | Fricker | 435/813 |
| 4,426,450 | 1/1984 | Donofrio | 435/255 |
| 4,743,451 | 5/1988 | Kalina | 426/15 |

FOREIGN PATENT DOCUMENTS 2118967 11/1983 United Kingdom ............... 435/161

OTHER PUBLICATIONS

Hoechst AG/Uhde GmbH Brochure, "The Novel Continuous Ethanol Process"; pp. 1-17, 1982.
Amerine, M. A., et al, The Technology of Wine Making, Westport, Com., AVI Publishing Company, Inc., 1980, pp. 196-197, TP548A48.

Primary Examiner—Robert A. Wax
Assistant Examiner—William H. Beisner
Attorney, Agent, or Firm—Vogt & O'Donnell

[57] ABSTRACT

A continuous fermentation process is performed in an apparatus system having at least two circulation fermenters arranged in a cascade. Fresh must is introduced into a first fermenter for fermentation with a flocculating yeast, growth of the yeast in the first fermenter being promoted by introduction of oxygen. The fermenting must and yeast are transferred from the first fermenter to a second fermenter and then to any subsequent fermenters of the cascade serially. In the second and any subsequent fermenters, the growth of yeast is inhibited. After passing through the last fermenter of the cascade, be it the second or a subsequent fermenter, yeast is separated from fermented must, and the separated yeast is removed from the system and is not recycled.

13 Claims, 1 Drawing Sheet

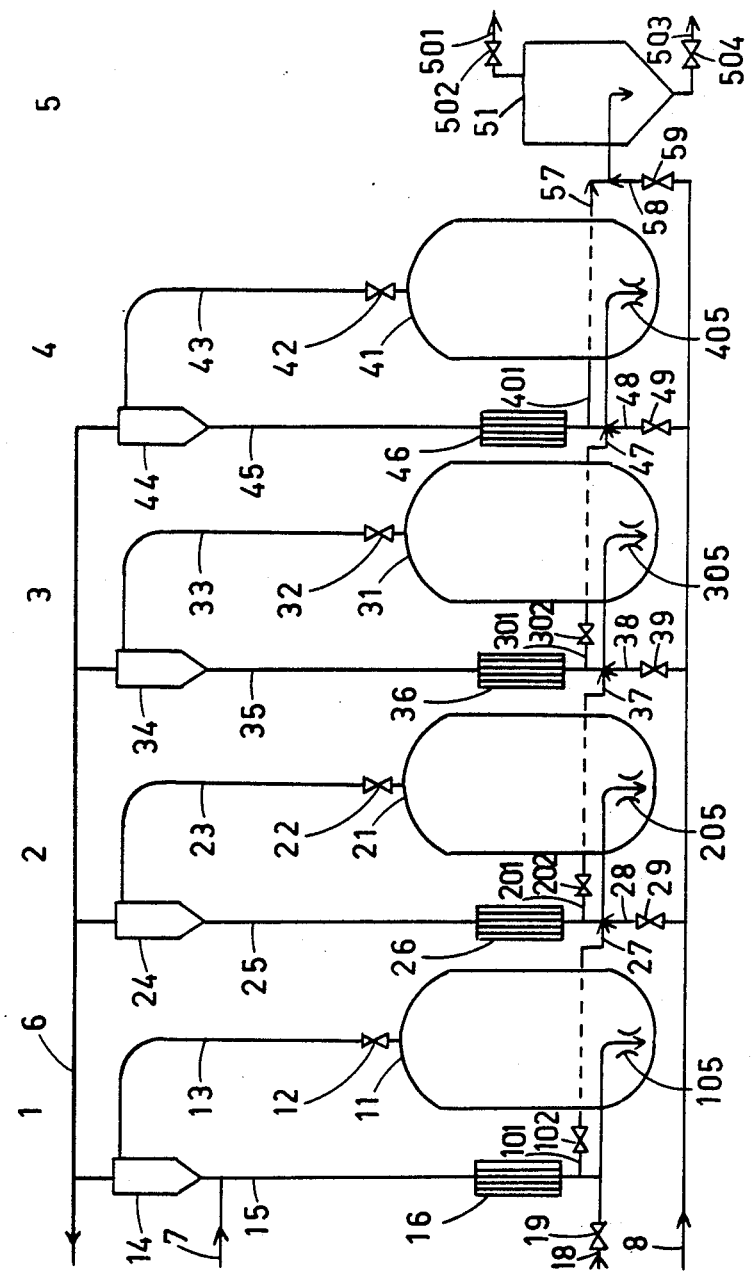

ALCOHOL PRODUCTION

BACKGROUND OF THE INVENTION

This invention relates to a process for the production of alcohol by continuous fermentation of a must in fermenters arranged in a cascade, in which fresh must and oxygen are continuously introduced at the beginning of the cascade and fermented must is continuously collected at the end of the cascade, and to an apparatus for the continuous production of alcohol comprising several fermenters arranged in a cascade.

There are various known processes and apparatus for the production of alcohol by fermentation of a culture medium rich in fermentable sugar which is referred to hereinafter as "must". Among the known processes, there are three main types which are discussed briefly hereinafter, namely, the batch process carried out in a single vat, the continuous process carried out in vats arranged in a cascade and the continuous process carried out in a circulation fermenter.

The batch process carried out in a single vat is still used today by virtue of its simplicity. Its principal disadvantage is its low productivity.

The continuous process carried out in vats arranged in a cascade, in which fresh must and oxygen are continuously introduced at the beginning of the cascade, in which the yeast circulates with the must from one vat to the other after having been produced or introduced into the first vat and in which fermented must is continuously collected at the end of the cascade, is no higher in its productivity than the single-vat batch process, but does avoid the interruptions in production and the need to clean the vat between two production batches.

The continuous process carried out in a circulation fermenter is distinguished by its high productivity due to the fact that it enables a high concentration of yeast, particularly flocculating yeast, to be used in the must. In this type of known process, the concentration of yeast in the must is kept at the desired value by recycling at least part of the yeast separated from the fermented must withdrawn. Now, the consequence of such recycling is a prolonged average residence time of the yeast in the fermenter.

SUMMARY OF THE INVENTION

The object of the present invention is to provide a process and an apparatus for the continuous production of alcohol by fermentation which are distinguished by high productivity while, at the same time, avoiding recycling of the yeast to ensure a short average residence time of the yeast in the must during the fermentation process.

To this end, the process according to the invention is characterized in that it uses a flocculating yeast, the growth of the yeast is promoted in a first circulation fermenter, the growth of the yeast is inhibited in at least one following circulation fermenter, the yeast is separated from the fermented must at the end of said cascade and the yeast separated is removed.

Similarly, the apparatus according to the invention is characterized in that it, comprises several circulation fermenters and a decanter arranged in a cascade.

It has surprisingly been found that it is thus possible to carry out fermentation with a high concentration of yeast in the must without any need to recycle the yeast separated from the fermented must to keep this concentration at the desired level. In particular, it has been found that the use of circulation fermenters arranged in a cascade makes it possible, on the one hand, to establish internal circulation conditions for the must in each fermenter which enable a flocculating yeast to be used and, on the other hand, to establish global circulation conditions for the must through said cascade which provide for adequate renewal of the yeast mass in each fermenter. These two forms of circulation, termed internal and global, may thus each be established and controlled substantially independently although, on the one hand, they are combined over the greater part of the internal circuit of each fermenter and, on the other hand, involve very different rates of flow of the must, namely a relatively high flow rate for the internal circulation and a relatively low flow rate for the global circulation.

In consequence of the foregoing, it has been found that it is thus possible to reduce the average residence time of the yeast in the must during the fermentation process to a few tens of hours while, at the same time, ensuring a productivity of the order of 20 g alcohol per hour and per litre of must in the apparatus.

The importance of the reduction in the average residence time of the yeast in the must may be gauged from the risk of contamination of the must by undesirable microorganisms. Although under certain traditional fermentation conditions, the growth rate of the majority of microorganisms is greatly reduced so that they are unable to contaminate the must, there are nevertheless microorganisms which are capable of multiplying from spores and capable of invading any fermentation installation in the space of three weeks to one month, for example. Accordingly, if it is desired to carry out fermentation continuously for long periods without running any risk of contamination, it is essential to reduce drastically the average residence time of the yeast int he must.

DETAILED DESCRIPTION OF THE INVENTION

To carry out the process according to the invention, fermentation is preferably carried out under a carbon dioxide pressure of at least 1 bar which has a favourable effect on the physiological activity of the yeast and on its flocculation capacity.

Yeast may be introduced into the fermenters at the beginning of the process and subsequently kept there in such a quantity that the must preferably has a yeast content of from 30 to 70 g dry weight per litre.

The greater part of the total quantity of yeast produced during the fermentation process may be produced in the first fermenter. To this end, fresh must containing from 70 to 100 g fermentable sugar per litre may be introduced into the first fermenter in a quantity of from 0.8 to 1.0 volume of fresh must per volume of must present in the fermenter and per hour, in other words at an hourly dilution rate of 0.8 to 1.0. In this way, the alcohol content of the must in the first fermenter is limited to a value of from 30 to 40 g/l which still permits the desired growth of the yeast.

The growth of the yeast in the first circulation fermenter may be promoted by introducing oxygen into that fermenter in a quantity equal to or slightly larger than the sole quantity of oxygen necessary for that growth and preferably in a quantity of from 0.05 to 0.15 ml oxygen at atmospheric pressure per g dry weight of yeast and per hour in the must to enable the oxygen to be completely absorbed by the must. The use of this sole minimal quantity of oxygen is made possible in particular by the effect of a periodic variation or pulsation of the oxygen concentration which the yeast encounters in the must due, in particular, to the internal circulation of the must in the fermenter.

The growth of the yeast in the following circulation fermenters may be inhibited, for example, by not introducing any oxygen and/or by limiting the concentration of assimilable phosphate in the must. There is in effect no need for aeration in the following fermenters. The oxygen remaining in the must and the intermediate metabolites produced in the first fermenter are sufficient for the production of alcohol by fermentation to continue in the following fermenters.

Thus, it is possible to introduce into each of said following fermenters, on the one hand, fresh must containing 150 to 250 g fermentable sugar per litre at an hourly dilution rate of 0.04 to 0.4 and, on the other hand, fermented must transferred from the preceding fermenter in an hourly quantity equal to the total hourly quantity of must introduced into this preceding fermenter. It is thus possible to increase the alcohol content of the must in said following fermenters progressively and to obtain an alcohol content of the must of 55 to 65 g/l at the end of the cascade.

Finally, the yeast may be separated from the fermented must by decantation at the end of the cascade. The yeast is preferably separated from the fermented must in a decanter under carbon dioxide pressure, the fermentation process being completed in this decanter. The yeast separated in the decanter, where it may convert the residues of fermentable sugar emanating from a last circulation fermenter into alcohol, is thus not recycled, but instead removed, thus radically limiting the average residence time of the yeast in the must. This average residence time is thus substantially equal to the quotient of the total quantity of yeast present in the fermenters and the decanter divided by the quantity of yeast produced per hour during the fermentation process. The average time which the fresh must introduced into the first fermenter takes to pass through said cascade is generally distinctly shorter than this average residence time of the yeast in the must, thereby improving the long-term stability of the process and apparatus according to the invention, i.e., their immunity to possible contamination by sporulating microorganisms.

The apparatus according to the invention is thus characterized in that it comprises several circulation fermenters and a decanter arranged in a cascade. The circulation fermenters may be of any type in which, on the one hand, the must is able to circulate in a closed circuit and, on the other hand, the conditions prevailing in a fermentation zone or vat enable a flocculating yeast to be used.

One type of circulation fermenter which lends itself particularly effectively to the construction of the apparatus according to the invention is that which comprises a fermentation vat surmounted by an airlift pump. In this type of fermenter, the must is able to circulate under the sole effect of the carbon dioxide released during the fermentation process. The carbon dioxide is kept in solution under pressure in the vat by a counter-pressure valve and exerts the pumping effect by expanding in the pipe or airlift pump situated above the valve. Oxygen may be introduced in minimal quantities, optionally in the form of a mixture with nitrogen and/or carbon dioxide, into the upper part of a return pipe which connects the top of the airlift pump to the bottom of the fermentation vat so that it is completely taken up by the must before entering the vat.

Thus, one preferred embodiment of the apparatus according to the invention is characterized in that each circulation fermenter comprises a fermentation vat, a counter-pressure valve at the top of the vat, an airlift pump above the counter-pressure valve and a return pipe connecting the top of the airlift pump to the lower part of the vat, the first fermenter comprising means for injecting gas into the upper part of said return pipe and each fermenter comprising means for introducing fresh and/or transferred must and means for transferring fermented must connected to the lower part of said return pipe, while the decanter comprises a decantation vat under pressure which is connected at its top to a pipe for the removal of fermented must and at its bottom to a pipe for emptying decanted yeast, the means for transferring fermented must from said last fermenter being connected to means for introducing fresh and/or transferred must connected to the decantation vat.

The number of circulation fermenters may be from 2 to 6 for example. Their volume may be considerable and is preferably between 50 $m^3$ and several hundred $m^3$. The vat preferably comprises a cylindrical central part, a hemispherical lower part or base and a hemispherical upper part. The horizontal section of said central part is preferably of such dimensions that the rate at which the must ascends in the vat is approximately 0.5-2 cm/s. The height of the airlift pump is preferably such that an excess pressure of at least 1 bar is still exerted in the upper part of the vat and a pressure of approximately 0.5 bar is available for circulating the must at a flow rate corresponding to approximately 5 to 10 times the volume of the fermenter per hour, overcoming the resistance of the circuit as a whole. A gas retention of approximately 35% in the airlift pump, for example, signifies a total height of the pump of at least about 15 meters.

The resistance of the circuit is due in particular to the heat exchanger, preferably of the tubular type, which has to be provided, for example in the return pipe, to maintain a temperature of approximately 30° to 35° C. in the fermentation vat with a temperature difference of no more than about 3° C. between the top and the bottom of the vat.

Finally, the vat of the decanter may comprise, for example, a cylindrical body closed on top by a flat or slightly convex cover and, at its bottom, by a conical base. The volume of this vat may be of the order of one third or one half of the volume of the fermentation vats.

BRIEF DESCRIPTION OF THE DRAWING

The apparatus according to the invention is described hereinafter with reference to the accompanying drawing which diagrammatically illustrates one embodiment thereof.

DETAILED DESCRIPTION OF THE DRAWING

In the embodiment illustrated in the drawing, the apparatus comprises four circulation fermenters 1, 2, 3 and 4 and a decanter 5 arranged in a cascade. Each circulation fermenter comprises a fermentation vat 11, 21, 31 and 41 hereinafter designated collectively as 11-41 having a cylindrical central part closed on top and underneath by hemispherical upper and lower parts.

Each vat 11-41 comprises at its top a counter-pressure valve 12, 22, 32 and 42 by which it communicates with an airlift pump 13, 23, 33 and 43 hereinafter designated collectively as 13-43 situated above the vat. Each airlift pump is a simple pumping column or pipe which, at its top, opens into a degassing unit 14, 24, 34 and 44 of the cyclone type.

The upper part of each cyclone is connected to a pipe 6 for the removal of carbon dioxide while its lower part is connected to a return pipe 15, 25, 35 and 45 hereinafter designated collectively as 15-45 which thus connects the top of the airlift pump 13-43 to the lower part of the vat 11-41.

The first fermenter comprises a gas injector in the form of a gas injection pipe 7 connected to the upper part of the return pipe 15. At its lower end, each return pipe 15-45 passes through a tube-type heat exchanger 16, 26, 36 and 46 hereinafter designated collectively as 16-46.

Each fermenter comprises means for introducing fresh and/or transferred must connected to the lower part of the return pipe 15-45 below the heat exchanger 16-46. For the first fermenter, these means comprise a pipe 18 for the introduction of diluted fresh must and a valve 19 for the introduction of diluted fresh must. For the following fermenters, these means comprise a pipe 27, 37 and 47 hereinafter designated collectively as 27-47 for the introduction of transferred must and a pipe 28, 38 and 48 for the introduction of fresh must connected to a supply pipe 8 for concentrated fresh must by a valve 29, 39 and 49 for the introduction of concentrated fresh must.

In addition, each fermenter comprises means for transferring fermented must connected to the return pipe below the heat exchanger 16-46. For the first three fermenters, these means comprise a transfer pipe 101, 201 and 301 for fermented must connected by a transfer valve 102, 202 and 302 to the pipe 27-47 for the introduction of transferred must of the following fermenter. For the last fermenter, these means consist of a single pipe 401 for the transfer of fermented must which is directly connected to a pipe 57 for the introduction of transferred must of the decanter 5.

Finally, each return pipe 15-45 opens into the lower part of the vat 11-41 through a mixing element 105, 205, 305 and 405 of the venturi type.

The decanter 5 comprises a decantation vat 51 under pressure with a cylindrical body closed on top by a flat cover and underneath by a conical base. The vat 51 is connected at its top, or cover, to a pipe 501 for the removal of fermented must by a removal valve 502. The vat 51 is connected at its base to an emptying pipe 503 by an emptying valve 504.

The decanter 5 also comprises means for the introduction of fresh and/or transferred must connected to the lower part of the cylindrical body of the decantation vat. These means comprise the pipe 57 for the introduction of transferred must of the last fermenter and a pipe 58 for the introduction of concentrated fresh must connected to the supply pipe 8 by an injection valve 59.

The following Example illustrates one embodiment of the process according to the invention for the production of alcohol by continuous fermentation.

EXAMPLE

To carry out continuous fermentation by the process according to the invention, an apparatus similar to that described above with reference to the accompanying drawing is used.

In this apparatus, the four fermenters each have a total volume of 100 m$^3$ and a total height of 24 m. The decanter has a volume of 50 m$^3$. The vats of the fermenters and the decanter have a diameter of 5 m.

After an initial starting phase during which the necessary quantity of flocculating yeast Saccharomyces cerevisiae CBS 2961 is introduced into and/or produced in the vats, the continuous fermentation process is carried out under the condition shown in the following Table:

TABLE

| Fermenter (no.) | 1 | 2 | 3 | 4 | Decanter |
|---|---|---|---|---|---|
| Quantity of fresh must introduced (m$^3$/h) | 90 | 28.8 | 23.4 | 16.2 | 4.5 |
| Fermentable sugar content of the fresh must introduced (g/l) | 85 | 181 | 181 | 181 | 181 |
| Rate of dilution by the fresh must introduced (h$^{-1}$) | 0.9 | 0.288 | 0.234 | 0.162 | 0.09 |
| Total hourly dilution rate (h$^{-1}$) | 0.9 | 1.188 | 1.422 | 1.584 | 3.260 |
| Must content in dry weight of yeast in the vats (g/l) | 36.1 | 36.0 | 35.4 | 34.9 | 60 |
| Average residence time of the yeast in the vats (h) | 11.6 | 8.9 | 8.2 | 8.0 | 7.5 |
| Alcohol content of the must (g/l) | 36.9 | 47.8 | 53.5 | 57.5 | 60 |
| Quantity of oxygen at atmospheric pressure introuced in the form of air (m$^3$/min) | 0.2 | — | — | — | — |
| Internal ciculation rate of the must (m$^2$/h) | 700 | 500 | 500 | 500 | — |

Under these conditions, the global circulation rate of the must, in other words the total flow rate in the apparatus, is 163 m$^3$/h. The total production of alcohol, including the alcohol recovered from the CO$_2$ removed by the cyclones, amounts to 9.63 t/h, which represents a productivity of 21.4 g alcohol per hour and per litre of total volume of the apparatus. The total quantity of yeast produced amounts to 400 kg/h which is removed in the form of 3.63 m$^3$/h of a suspension containing 110 g dry weight of yeast per litre.

The fermentation process may thus carry on for several months without any risk of contamination by a sporulating microorganism.

I claim:

1. A continuous fermentation process for the production of alcohol without recycling of yeast comprising fermenting must with a flocculating yeast in an apparatus system having at least two circulation fermenters arranged in a cascade and having a decanter for separating yeast and must, continuously introducing a fresh must into a first fermenter containing flocculating yeast and introducing oxygen into the first fermenter in an amount necessary for promoting growth of the yeast in the first fermenter, transferring the fermenting must and yeast from the first fermenter to each subsequent fermenter in the cascade serially and inhibiting the growth of the yeast in each subsequent fermenter to which the fermenting must and yeast are transferred, collecting fermented must and yeast in the decanter from a last fermenter in the cascade, separating the collected fermented must and yeast by decantation and removing the separated yeast from the system, wherein the yeast has an average residence time int he must which is substantially equal to a quotient of a total quantity of yeast present in the fermenters and the decanter divided by a quantity of yeast grown per hour in the system and wherein an average time in which the must introduced into the system into the first fermenter as fresh must takes to pass through the fermenters of the cascade is shorter than the average residence time of the yeast in the must.

2. A process according to claim 1 wherein the growth of the yeast is inhibited by not introducing oxygen into the fermenters subsequent to the first fermenter.

3. A process according to claim 1 wherein the growth of the yeast is inhibited by limiting a concentration of assimilable phosphate in the fermenting must int he fermenters subsequent to the first fermenter.

4. A process according to claim 1 wherein the growth of the yeast is inhibited by not introducing oxygen and by limiting a concentration of assimilable phosphate in the fermenting must in the fermenters subsequent to the first fermenter.

5. A process according to claim 1 wherein there are from three to six fermenters.

6. A process according to claim 1 further comprising maintaining a carbon dioxide pressure of at least 1 bar in each fermenter.

7. A process according to claim 1 wherein the fermenting must has a yeast content in an amount of from 30 g dry weight/l to 70 g dry weight/l.

8. A process according to claim 1 wherein the fresh must has a fermentable sugar content of from 70 g/l to 100 g/l and is introduced into the first fermenter in an amount of from 0.8 to 1.0 by volume of fresh must per volume of fermenting must present in the first fermenter per hour.

9. A process according to claim 1 wherein from 0.5 ml to 0.15 ml of oxygen at atmospheric pressure per g dry weight of yeast int he fermenting must in the first fermenter is introduced into the first fermenter per hour.

10. A process according to claim 1 further comprising introducing fresh must having a fermentable sugar content of from 150 g/l to 250 g/l into each fermenter subsequent to the first fermenter in a quantity of from 0.04 to 0.4 by volume of fresh must per volume of fermenting must present in each subsequent fermenter per hour and wherein the fermenting must is transferred from each preceding to each subsequent fermenter in an amount equal to the quantity of fresh must introduced into the preceding fermenter.

11. A process according to claim 1 wherein the fermenting must in the first fermenter has an alcohol content in an amount of from 30 g/l to 40 g/l be weight.

12. A process according to claim 2 wherein the fermented must separated from the yeast has an alcohol content in an amount of from 55 g/l to 65 g/l by weight.

13. A process according to claim 1 wherein the collected yeast and fermented must are separated by decantation under carbon dioxide pressure.

* * * * *